United States Patent
Bredno et al.

(10) Patent No.: US 9,636,079 B2
(45) Date of Patent: May 2, 2017

(54) MOTION LAYER DECOMPOSITION CALIBRATION OF X-RAY CT IMAGERS

(71) Applicant: KONINKLIJKE PHILIPS N.V., Eindhoven (NL)

(72) Inventors: Joerg Bredno, San Francisco, CA (US); Eberhard Sebastian Hansis, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 244 days.

(21) Appl. No.: 14/401,130

(22) PCT Filed: May 16, 2013

(86) PCT No.: PCT/IB2013/054003
§ 371 (c)(1),
(2) Date: Nov. 14, 2014

(87) PCT Pub. No.: WO2013/182928
PCT Pub. Date: Dec. 12, 2013

(65) Prior Publication Data
US 2015/0103972 A1    Apr. 16, 2015

Related U.S. Application Data

(60) Provisional application No. 61/655,602, filed on Jun. 5, 2012.

(51) Int. Cl.
*A61B 6/03*   (2006.01)
*A61B 6/00*   (2006.01)
(Continued)

(52) U.S. Cl.
CPC ............ *A61B 6/584* (2013.01); *A61B 6/4035* (2013.01); *A61B 6/42* (2013.01); *A61B 6/4233* (2013.01);
(Continued)

(58) Field of Classification Search
CPC ......... A61B 6/032; A61B 6/4035; A61B 6/42; A61B 6/4233; A61B 6/4441; A61B 6/58; A61B 6/582; A61B 6/583; A61B 6/584
(Continued)

(56) References Cited

U.S. PATENT DOCUMENTS 4,288,695 A * 9/1981 Walters .................. A61B 6/032
                                                        378/159
6,044,132 A * 3/2000 Navab .................. A61B 6/4441
                                                        378/163
(Continued)

FOREIGN PATENT DOCUMENTS

JP          2010246715 A       4/2010

*Primary Examiner* — Allen C. Ho

(57) ABSTRACT

An x-ray computed tomography system (14) includes a gantry (15), a plurality of elements (18), and one or more processors (28). The gantry (15) moves to different orientations and generates x-ray data which includes image projection data at a plurality of the orientations. The plurality of elements (18) connect to the gantry and cause x-ray attenuation of the generated projection data. The one or more processors (28) are programmed to receive (60) the generated x-ray data and decompose (62) the received image projection data into indications of relative positions of the plurality of elements at different orientations of the gantry.

20 Claims, 5 Drawing Sheets

(51) Int. Cl.
*G06T 11/00* (2006.01)
*G01N 23/04* (2006.01)
*G21K 1/02* (2006.01)
*G21K 1/04* (2006.01)

(52) U.S. Cl.
CPC .......... *A61B 6/4441* (2013.01); *A61B 6/5205* (2013.01); *A61B 6/58* (2013.01); *A61B 6/582* (2013.01); *A61B 6/583* (2013.01); *G01N 23/046* (2013.01); *G06T 11/005* (2013.01); *G21K 1/025* (2013.01); *G21K 1/04* (2013.01); *A61B 6/032* (2013.01); *G06T 2211/412* (2013.01)

(58) Field of Classification Search
USPC .......................................... 378/207; 382/131
See application file for complete search history.

(56) References Cited

U.S. PATENT DOCUMENTS

| | | | | |
|---|---|---|---|---|
| 6,092,928 | A * | 7/2000 | Mattson | A61B 6/08 378/197 |
| 6,379,043 | B1 * | 4/2002 | Zylka | G01N 23/04 378/164 |
| 6,471,399 | B1 * | 10/2002 | Zylka | A61B 6/583 378/207 |
| 6,491,430 | B1 * | 12/2002 | Seissler | A61B 6/4405 348/E5.086 |
| 6,533,455 | B2 * | 3/2003 | Graumann | A61B 6/547 378/205 |
| 6,851,855 | B2 * | 2/2005 | Mitschke | A61B 6/547 378/205 |
| 6,950,492 | B2 * | 9/2005 | Besson | A61B 6/508 378/16 |
| 7,010,095 | B2 * | 3/2006 | Mitschke | A61B 90/36 378/162 |
| 7,016,456 | B2 | 3/2006 | Basu et al. | |
| 7,065,393 | B2 * | 6/2006 | Sati | A61B 6/08 378/197 |
| 7,147,373 | B2 * | 12/2006 | Cho | A61B 6/547 378/164 |
| 7,224,763 | B2 * | 5/2007 | Naidu | G01N 23/046 378/210 |
| 7,391,844 | B2 * | 6/2008 | Wu | A61B 6/032 378/18 |
| 7,648,275 | B2 | 1/2010 | Reboni et al. | |
| 7,927,014 | B2 * | 4/2011 | Dehler | A61B 6/12 378/2 |
| 7,950,849 | B2 * | 5/2011 | Claus | G06T 11/005 378/18 |
| 8,043,003 | B2 * | 10/2011 | Vogt | G01N 23/046 378/207 |
| 8,104,957 | B2 * | 1/2012 | Maier | A61B 6/4441 378/205 |
| 8,104,958 | B2 * | 1/2012 | Weiser | A61B 6/583 378/162 |
| 8,262,288 | B2 * | 9/2012 | Shaughnessy | A61B 6/032 378/154 |
| 8,315,352 | B2 * | 11/2012 | Wu | A61B 6/032 378/18 |
| 8,374,678 | B2 * | 2/2013 | Graumann | A61B 6/12 378/205 |
| 8,611,627 | B2 * | 12/2013 | Wu | A61B 6/032 382/131 |
| 8,958,524 | B2 * | 2/2015 | Subramanian | G01T 7/005 378/207 |
| 9,042,624 | B2 * | 5/2015 | Dennerlein | G06T 11/008 382/131 |
| 2006/0245628 | A1 | 11/2006 | Jeung et al. | |
| 2007/0172033 | A1 | 7/2007 | Gorges et al. | |
| 2008/0186311 | A1 | 8/2008 | Claus | |
| 2011/0176663 | A1 | 7/2011 | Shaughnessy | |

* cited by examiner

MOTION LAYER DECOMPOSITION CALIBRATION OF X-RAY CT IMAGERS

CROSS REFERENCE TO RELATED APPLICATIONS

This application is a national filing of PCT application Serial No. PCT/IB2013/054003, filed May 16, 2013, published as WO 2013/182928 A1 on Dec. 12, 2013, which claims the benefit of U.S. provisional application Ser. No. 61/655,602 filed Jun. 5, 2012, which is incorporated herein by reference.

The following relates generally to x-ray computed tomography. It finds particular application in conjunction with scanner calibration and image artifact compensation, and will be described with particular reference thereto. However, it will be understood that it also finds application in other usage scenarios and is not necessarily limited to the aforementioned application.

X-ray computed tomography systems such as cone-beam computed tomography (CBCT), 3D rotational angiography (3DRA), x-ray CT (XCT), interventional x-ray, C-arm and the like, emit x-rays and detect the emitted x-rays after passing through a subject in order to reconstruct images. Air calibration or rotational gain calibration projection images are typically collected at each of a plurality of gantry positions without a subject and stored for the uniformity correction for the corresponding position. The uniformity correction data stored for each gantry position is used in image reconstruction. The air calibration determines x-ray attenuation and intensity changes not caused by the subject, but by elements of the scanner and other sources. The air projection image of a theoretical, ideal imaging system at each gantry angle is a uniform blank image. In practice, the air projection images include non-uniformities from attenuating structures in the beam path, non-uniform illumination by the x-ray source, non-uniform detector sensitivity, and the like. When the patient is imaged these non-uniformities are superimposed on the absorption profile of the patient. The non-uniformities are compensated by normalizing the patient projection image at each gantry angle with the air projection image at the same gantry angle to produce corrected patient projection images. The corrected projection images from a plurality of gantry angles around the patient can be reconstructed into a 3D image.

As CT systems evolve with more open systems such as C-arm systems and simpler, less rigid gantries, a change in the non-uniformities (and the respective air projection images) both within one acquisition and between different acquisitions can be observed. The changes are not necessarily reproducible. Some changes of air projection images in the open systems are attributable to elements which move relative to each other. For example, an element located on one arm can move different than an element on another arm. A source at one end can move different than a detector at the other end. With system wear, arm movement, accidental impact, thermal expansion/contraction, and other environmental factors, individual elements even on the same arm can move relative to each other. For example, even though an anti-scatter grid is fixed to a detector, a tilt in the detector causes a change of the shadows induced by the lamellae of the grid. The differing changes in position can occur with each movement, which can lead to uncompensated image artifacts and inaccurately reconstructed absorption coefficients when imaging a subject. The air calibrations which correct for attenuation and intensity changes due to scanner elements may not remain valid from a time of generating the air calibration to a time of imaging the patient.

The following discloses a new and improved system and method of tomographic image calibration which addresses the above referenced issues, and others.

In accordance with one aspect, an x-ray computed tomography system includes a gantry, a plurality of elements, and one or more processors. The gantry moves to different orientations and generates x-ray data which includes image projection data at a plurality of the orientations. The plurality of elements connect to the gantry and cause x-ray attenuation of the generated projection data. The one or more processors are programmed to receive the generated x-ray data and decompose the received image projection data into indications of relative positions of the plurality of elements at different orientations of the gantry.

In accordance with another aspect, a method of x-ray computed tomography calibration includes receiving x-ray data which includes image projection data at each of a plurality of gantry orientations around an imaging region. The received image projection data is decomposed to derive relative positions of a plurality of elements at one or more gantry orientations, each of the elements causing x-ray attenuation attributable to the elements in the received image projection data. A correction of measured attenuation is generated based on the relative positions of the plurality of elements.

In accordance with another aspect, an x-ray computed tomography system includes a rotatable gantry, a memory, a decomposition unit, and a correction unit. The rotatable gantry carries elements which include an x-ray source, an x-ray filter, a shutter/collimator, an x-ray detector, and an anti-scatter grid, and the gantry moves to different orientations. The memory stores attenuation contributions attributable to each of the elements. The decomposition unit decomposes air scan projection images at the different orientations into relative positions of each of the elements. The correction unit adjusts the correction of attenuation to projection image data based on the relative positions of the each of the elements.

One advantage is artifact reduction.

Another advantage resides in dynamic artifact compensation which dynamically adjusts during an imaging session.

Another advantage resides in a post processing technique for correcting artifacts due to scanner element movement.

Another advantage resides in more accurately reconstructed absorption coefficients.

Another advantage resides in the incorporation into existing systems and procedures.

Another advantage resides in flexibility in adapting to existing and new more open CT gantry designs.

Still further advantages will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

FIG. 1 diagrammatically illustrates elements of an exemplary prior art X-ray imaging system.

Figure 4:
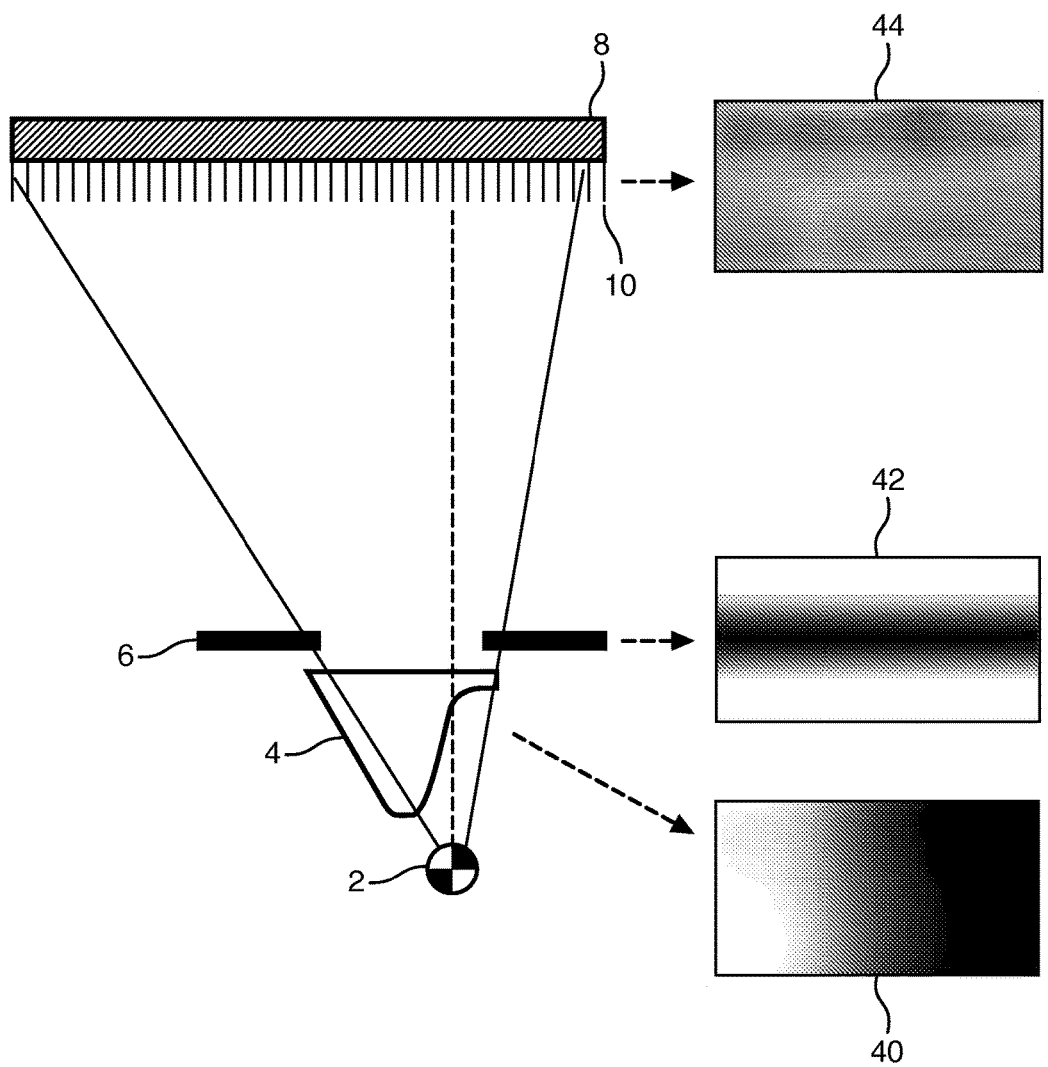

FIG. 4 diagrammatically illustrates in one embodiment imaging data after decomposition in multiple layers containing attenuation and non-uniformity caused by individual system components.

Figure 5:
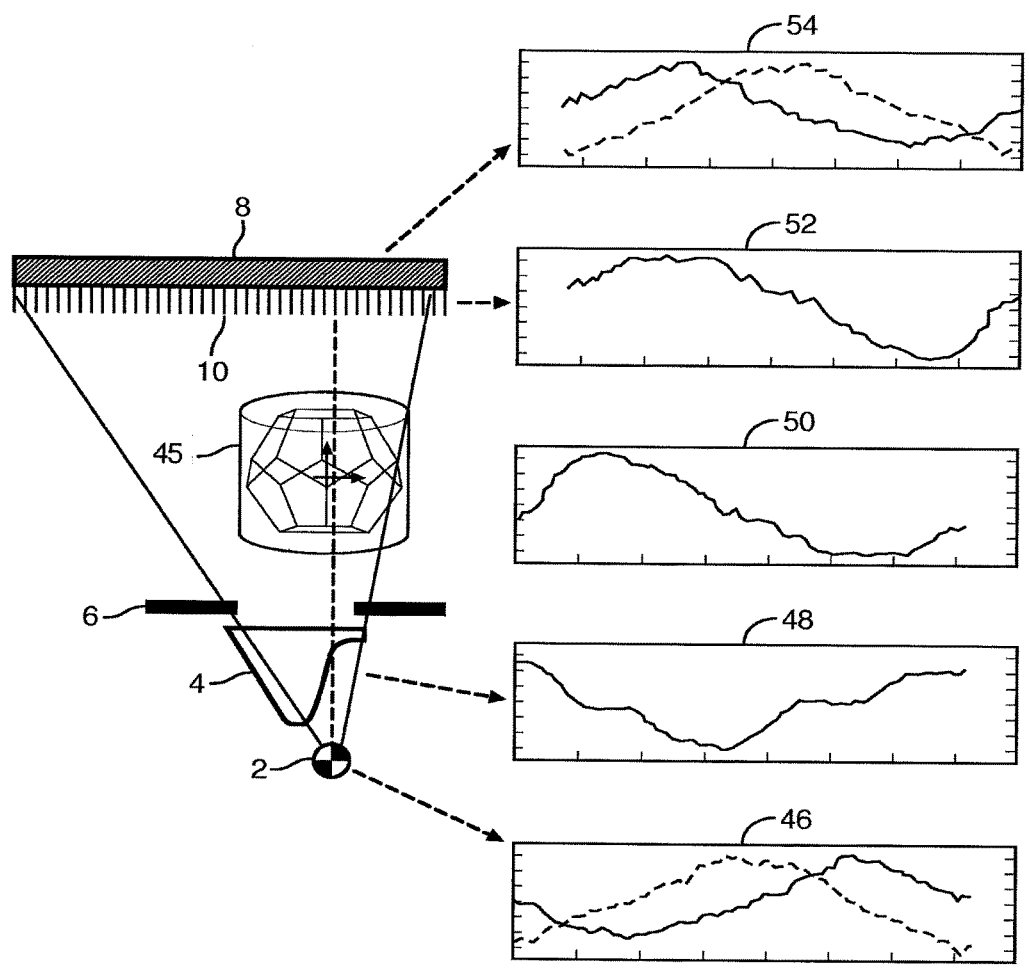

FIG. 5 diagrammatically illustrates an embodiment of the system and decomposed system element motion.

Figure 6:
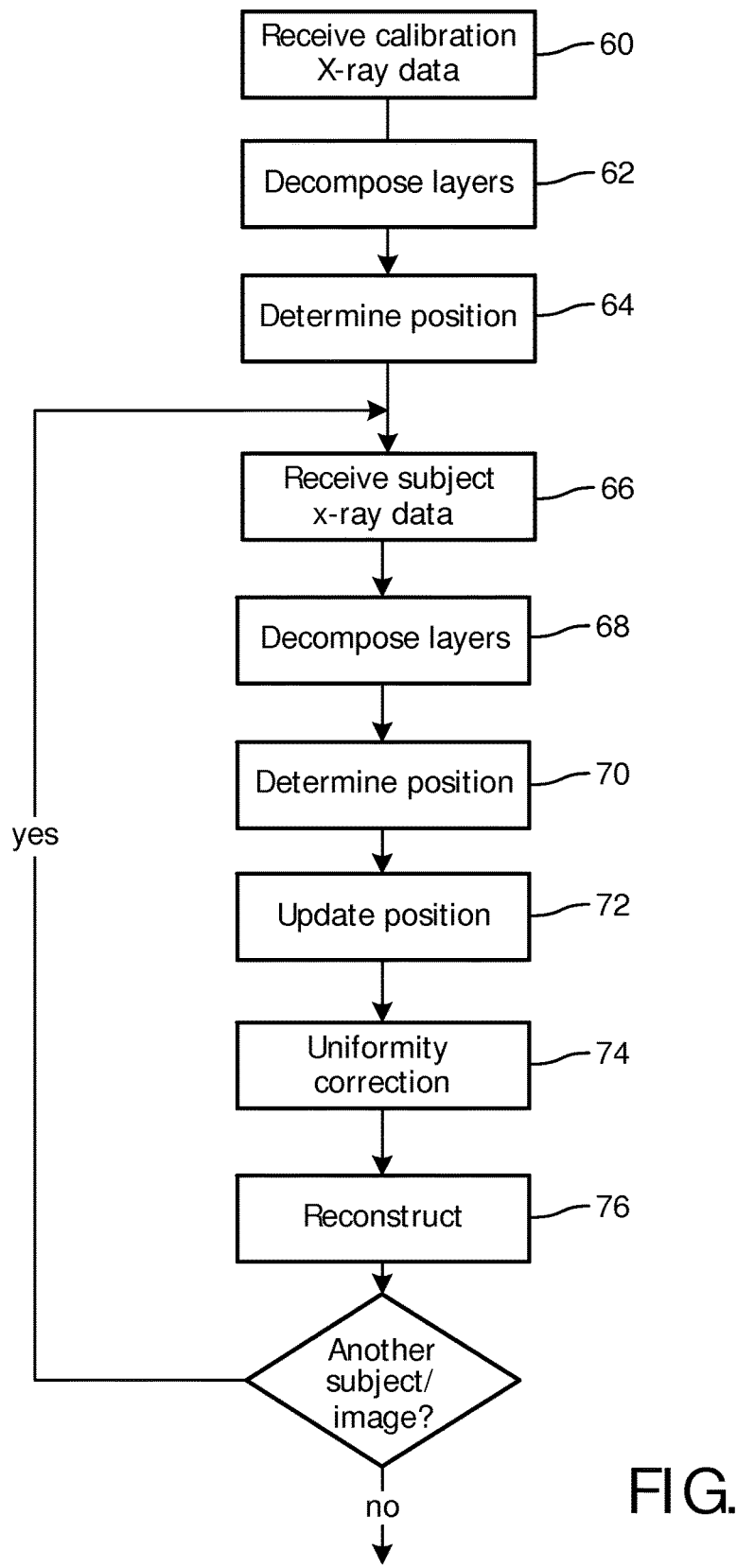

FIG. 6 flowcharts one method of using an embodiment of the system.

Figure 1:
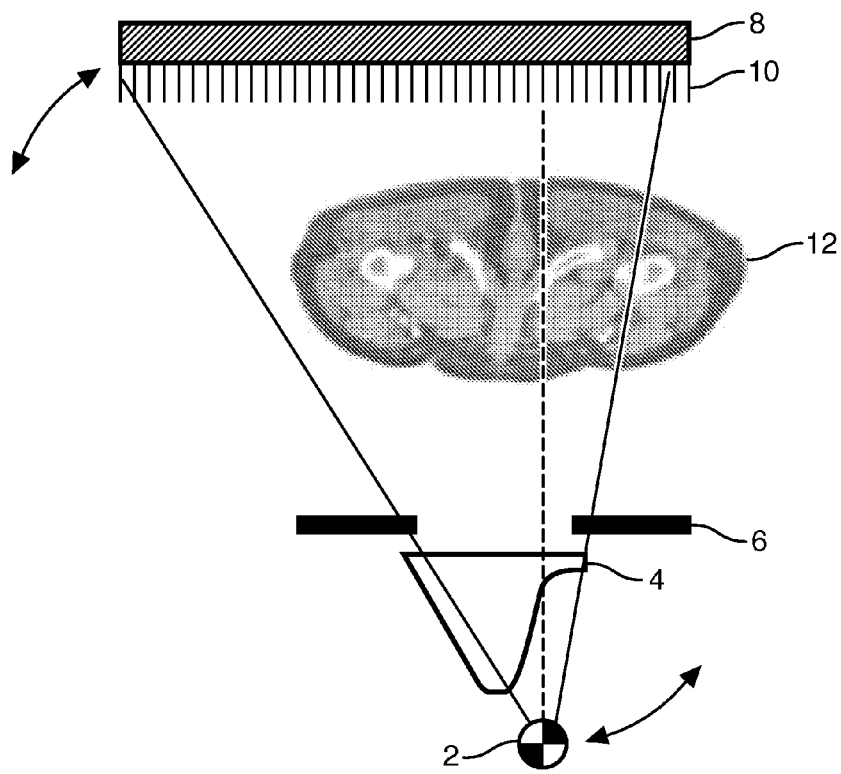

With reference to FIG. 1, a typical flat panel x-ray computed tomography system includes an x-ray source 2, an x-ray filter 4, a shutter/collimator 6, an x-ray detector 8 and an anti-scatter grid 10. The x-ray source 2 such as an x-ray tube anode emits x-rays. The x-ray filter 4 includes a beam shaper or filtration unit which filters the x-rays. The shutter/collimator 6 defines the extent of the beam of x-rays which pass through the subject 12 and impact the x-ray detector 8. The x-ray source 2, the x-ray filter 4 and the shutter/collimator 6 are typically located on one arm or at the end of an arm of the flat-panel x-ray computed tomography system. However, other geometries, such as a ring, and the like are also contemplated. After passing through the subject 12 the x-rays pass through an anti-scatter grid 10 and are detected by an x-ray detector 8. The x-ray detector 8 and anti-scatter grid 10 are typically located opposite the x-ray source 2, the x-ray filter 4 and the shutter/collimator 6 such as on another arm or the other end of the arm of the flat-panel x-ray computed tomography system. The shutter/collimator 6 typically limits the cross section of the x-ray beams to the cross section of the x-ray detector 8 or to an anatomical region of interest to limit the patient's exposure to x-rays. The x-ray detector 8 detects the x-rays passed through the subject 12 in the field of view. The x-ray detector 8 typically includes an array of detector elements which detect x-rays in areas each corresponding to a pixel. The anti-scatter grid 10 such as an assembly of lamellae or plates, typically perpendicular to the detector surface, limits the impact of scatter in images.

Figure 2:
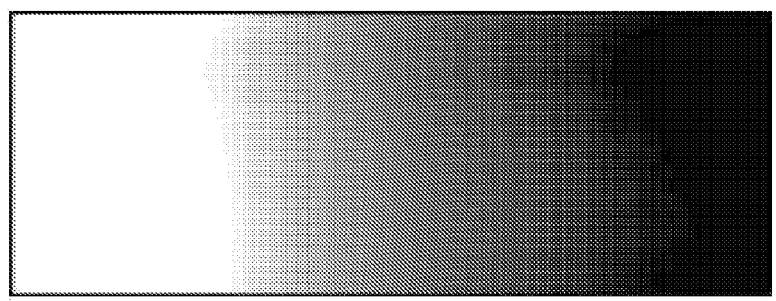
FIG. 2 shows an exemplary air calibration projection image at one gantry position of the system of FIG. 1.

With reference to FIG. 2, a projection image at one gantry position of a typical air calibration scan is shown. The air calibration scan measures at each detector element or pixel, the intensity of the x-ray received from the x-ray source 2. The air calibration projection images are generated for a number of gantry orientations. The projection image of FIG. 2 shows a darken area on the right where the x-ray filter 4 is thinnest and the x-rays are most intense. The light area to the left indicates the thickest portion of the x-ray filter 4 where the x-rays are the least intense. Although difficult to discern, the air calibration image has a series of evenly spaced thin white lines where the lamellae of the anti-scatter grid block 10 the x-rays and cast shadows on the x-ray detector 8. The air projection image is representative of an off-center x-ray detector 8 such as FIG. 1. An air calibration projection image from a system with a symmetric x-ray detector 8 would show light areas at both ends with the intense area centered.

Figure 3:
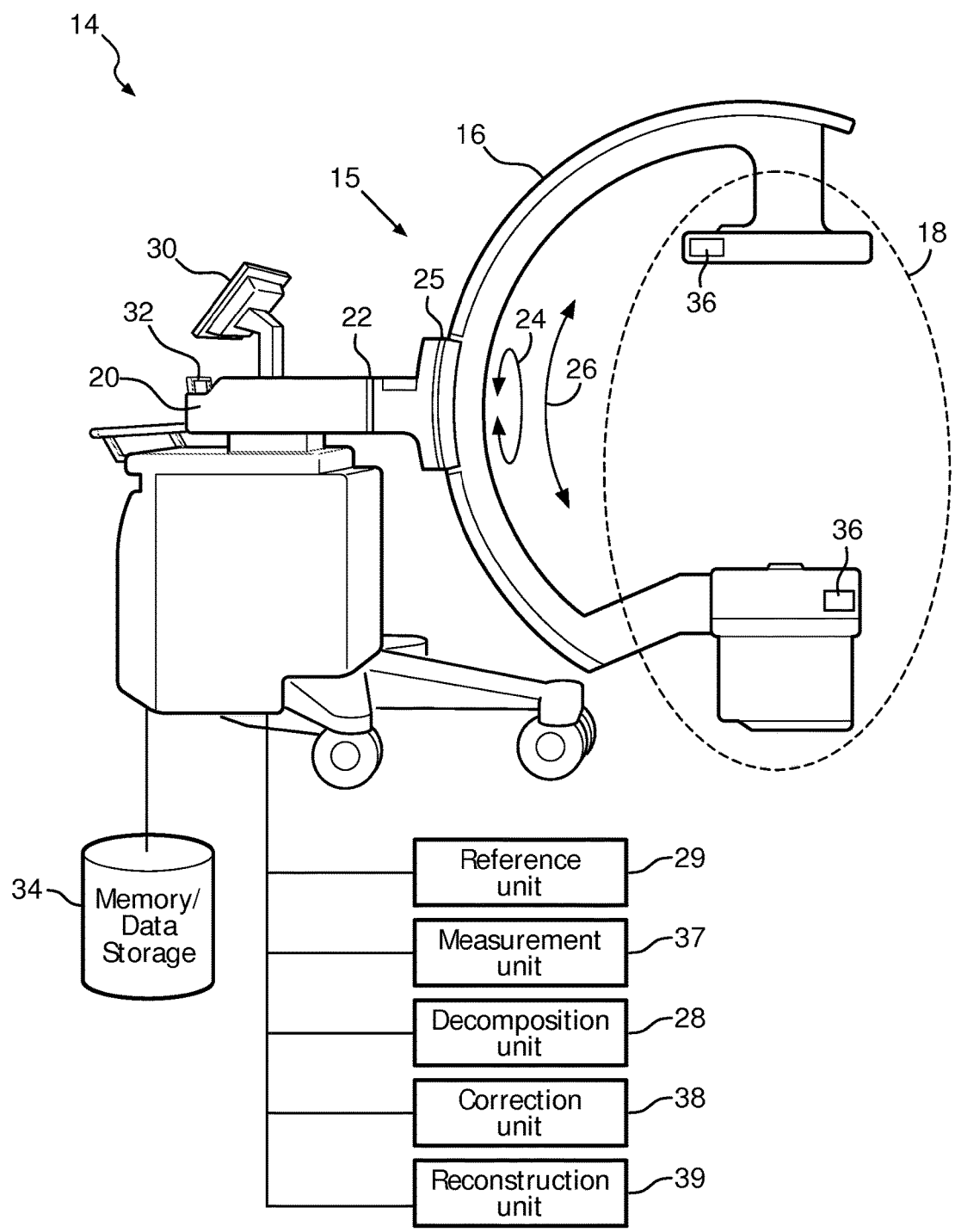
FIG. 3 depicts an embodiment of a C-arm imaging system.

With reference to FIGS. 3 and 4, a C-arm embodiment of the system 14 is shown. The system includes a gantry 15, which in this example includes a "C" shaped arm 16. The system includes elements 18 disposed at opposite ends of the C-arm 16. The system elements 18 include the x-ray source 2, the x-ray filter 4, the shutter/collimator 6 disposed at one end, and the x-ray detector 8 and anti-scatter grid 10 disposed at the opposite end. The C-arm 16 is attached to a horizontal arm 20 which has a pivot 22. A drive (not visible) rotates the C-arm 16 along a trajectory 24 around an axis of the pivot to move the x-ray source 2 and x-ray detector 8 assemblies typically by 360° around an imaging area between opposite ends of the C-arm 16. The region of the patient to be imaged is supported on a patient table or support in the imaging area. The C-arm 16 is mounted in a slide 25 in the horizontal arm 20 which carries a drive (not visible) for moving the C-arm 16 along a trajectory 26 to selectively image the subject over about 180° of projection directions. Calibration information is obtained by processing one or more calibration acquisitions. The calibration information is used to correct images acquired during the scan of a subject such as in the creation of tomographic cross-sectional images.

The system elements 18 generate and detect x-rays which pass through the imaging area. The x-rays detected by the x-ray detector 8 are communicated to a decomposition unit 28 connected via circuitry in the gantry 15. The decomposition unit 28 can be embodied by one or more processors. During the air calibration scan, x-ray data is received by the system elements 18 and transmitted to the decomposition unit 28. The decomposition unit 28 uses air scan acquisitions and optionally processing results from geometric phantom acquisitions to decompose a selection of projection images into relative positions of each of the elements 18 for the different gantry orientations. The relative positions are based on ideal positions in a system 14 with no deformation or misalignment compared to their target position obtained from design information. A reference unit 29 stores and maintains the reference images and other data such as design information, system maintenance information, and the like. The system 14 includes a display device 30 and at least one input device 32. A healthcare practitioner can control the operation of the system 14 through the input device 32. The display device 30 displays the images, menus, panels, and user controls and includes one or more of a LCD display, an LED display, a plasma display, a projection display, a touch screen display, and the like. The display device 30 and the input device 32 can operate as part of a computer such as a desktop computer, a laptop, a tablet, a mobile computing device, a smartphone, and the like. The input device 32 can be a keyboard, a mouse, a microphone, and the like. The system 14 can include a storage device 34 such as memory, disk, network attached storage and the like.

Reference scans including projection images are stored and maintained by the reference unit or memory 29. During a scan of a subject, x-ray projection data is received by the x-ray detector 8 and transmitted to the correction unit 38. One or more sensors 36 provide data with the x-ray projection data such as operating temperatures, strain measurements, gantry positional measurements, wear measurements and the like. Optionally, such a sensor can be implemented by an analysis of the x-ray projection data to determine and update positional measurements. The measurement unit 37 receives the measurement data and determines the relative positions of each of the elements 18 based on the measured data. Other data can be included with the x-ray projection data from the reference unit 29 such as expected mechanical drift based on history of the system 14 or system type, engineering specifications, manufacturer based reference scans, and the like. A correction unit 38 generates a correction for each position for each of the system elements 18. The correction unit 38 can store the generated corrections in the storage device 34 or calculate them in real time or retroactively. The corrections for each gantry orientation and each element 18 can include overlays or vector translations for each element 18 or portion of an element 18 typically expressed in detector pixels, intensity adjustments, and the like. The combined corrections form a uniformity correction. A reconstruction unit 39 reconstructs images using the received x-ray data which includes projection data, sensor data, and the like from the decomposition unit 28 and corrected by the correction unit 38. The uniformity correction can be generated as an entire or relative adjustment by the correction unit 38. During image reconstruction, the reconstruction unit 39 uses a uniformity correction based on the combined corrections of each element 18 for the different gantry orientations from the correction unit 38.

The various units are suitably embodied by an electronic data processing device, such as the electronic processor or electronic processing device of the decomposition unit 28, or by a network-based server computer operatively connected with the system 14 by a network, or so forth. Moreover, the disclosed calibration techniques are suitably implemented as a non-transitory storage medium storing instructions (e.g., software) readable by an electronic data processing device and executable by the electronic data processing device to perform the disclosed calibration techniques.

FIG. 4 diagrammatically illustrates one embodiment of image projection data used to decompose system element motion. Acquired air scan calibration projection images such as shown in FIG. 2 are decomposed into calibration projection images for each element such as a filter air scan projection image 40, a shutter air scan projection image 42, and an anti-scatter grid air scan projection image 44. The decomposition makes use of known image processing techniques, taking known properties of the system elements 18 into account, such as their spatial scale or repeated spatial patterns. Alternatively, separate air scan projection images of the system elements 18 can be created as part of the initial manufacturing process. The separate calibration images can then be updated from the decomposition of air scan calibration projection images, e.g. daily, before each patient, etc.

In an example image, the air filter scan projection image 40 shows the non-uniform nature of the x-ray filter 4. The illustrated x-ray filter 4 is asymmetric and shows a greater intensity on the right which tapers to the left and tapers most strongly to the lower left. An example shutter air scan projection image 42 shows the intensity greatest in the center. Although not readily visible to the normal eye, inconsistencies in the edges of the shutter/collimator 6, if present, are revealed in the image. The anti-scatter grid air scan projection image 44 shows uniformly spaced lines where the lamellae or grid cast shadows on the x-ray detector 8. Shifting of the lamellae relative to the x-ray detector 8 or shifting of the x-ray source 2 relative to the lamellae the lines. Moreover, if the shift causes misalignment of the lamellae with the x-ray source 2, the lines get wider and the overall throughput of radiation through the scatter grid 10 is reduced non-uniformly over the x-ray detector 8. In the decomposition, each element 18 is separated or decomposed using sensor information for its current position. For example, when this sensor is implemented using image analysis, then a least squares error minimization can be used to determine the relative placement and orientation of the lamellae based on the individual pixels values of an initial air scan calibration projection images and/or the known geometry of the scatter grid 10 and a subsequent air scan at different gantry positions. The multi-layer decomposition measures the detected position of the anti-scatter grid based, for example, on the lines and shadows in the air scan calibration projection image. Similar decomposition is performed for the x-ray filter 4 and shutter/collimator 6.

FIG. 5 diagrammatically illustrates an embodiment of the system 14 and decomposed system element motion. A geometric phantom 45 is used to calibrate the positions of some elements 18 such as the x-ray source 2 and x-ray detector 8 elements, e.g., relative to an isocenter of the scanner. The information from a geometric phantom 45 can be used to further refine or correct the relative positions of each element 18. For example, an anti-scatter grid 10 is firmly attached to the x-ray detector 8, but the anti-scatter grid 10 can change its location relative to the focal spot of the x-ray source 2. In another example, the x-ray filter 4 or beam shaper is attached to the tube or the x-ray source housing with mechanics of known degrees of freedom and positioning accuracy. The movement of each element 18 relative to a center can be determined from the data such as the air scan calibration projection images, geometric calibration projection images, imaging of a subject, sensors, etc. For example, image features from imaging of a subject can be measured that capture the position of the individual elements 18. Artifact effects such as due to the anti-scatter grid lamellae, the beam shaper profile, or the collimator edges can be removed from the image.

The decomposition can be shown graphically for each element 18 with the y-axis as the deviation from the ideal center or offset, and the x-axis representing the gantry rotation angle determined from a variety of sources such as positional sensors, geometric phantoms, and the like. Note: source graph 46, filter graph 48, collimator/shutter graph 50, anti-scatter grid graph 52, and detector graph 54 of FIG. 5.

With reference again the FIG. 4, before imaging a patient or in regular service intervals, the air calibration scan and the geometric calibration scan are conducted. Air and geometric projection images are generated at each angular step, performing the geometric calibration scan first and the air calibration scan after removing the geometric calibration phantom from the x-ray system. The air projection images at each angular step or a subset of angular steps are stored in a memory 34. Alternatively, ideal air projection images of each system element are generated using system knowledge and image simulation methods. Geometric calibration information, i.e., the positions of the x-ray source and detector relative to an isocenter for each requested gantry position, are derived from the geometric calibration scan and stored as well. For each angular step, one or more reference images representing one or more system elements are selected from the ideal air projection images, the subset of air projection images stored in memory 34, or the air projection image acquired at this angular step.

The decomposition unit 28 generates calibration data. The decomposition unit 28 uses image processing analysis methods to determine the combination of air projection images for each system element and geometric transformations of these air projection images that best represent the air projection image acquired at each angular step. The determined combination of air projection images and geometric transformations are used to generate calibration data. The calibration data can be stored as a set of one or more air calibration projection images for each system element as shown in FIG. 4 together with the geometric transformations for each angular step. The determined parameters of the geometric transformation and their change over the course of a gantry rotation are represented by the graphs in FIG. 5. To correct projection data from the acquisition of a subject, the correction unit 38 selects the air projection images for each system element and gantry position, executes the geometric transformations determined by the decomposition unit 28 during calibration, and performs the uniformity correction of the subject projection images with these correction images.

The geometric transformation parameters can be obtained during calibration and updated during subject imaging using data obtained from external sensors or the subject imaging itself. The differences between geometric transformation parameters during calibration and during the acquisition of a subject can be determined using other measurements. The element positions are a function of the reference measurement and the difference between the reference image and the images at each gantry orientation. For example, an increase in operating temperature of the arm may cause expansion which causes a difference in relative movement of an element. System wear on the lateral track may change the relative position of elements depending on the weights of elements on each arm. System wear can be considered in the differences between the reference image and the images at each orientation or can include measured system wear from sensors, operational time tables and the like. The positional adjustments to the reference image at each orientation can be stored in memory. The correction unit 38 or processor receives the shift or positional change information from the decomposition unit 28, combines the attenuation corrections attributable to each element, e.g. the inverse of images with adjustments based on current measurements. The correction unit adjusts the reference uniformity correction accordingly and stores it in a memory.

When the patient is scanned, projection images are generated at one or more gantry orientations. The air scan correction corresponding to the gantry orientation is retrieved from the memory by the reference unit or recalculated by the correction unit using the current information from the measurement unit. The correction can be improved by determining relative shifts of system components from the projection images of the patient scan and using those shifts to generate more accurate correction images. The correction improvement uses known image processing methods which take the known geometrical characteristics of the system components into account.

The uniformity correction projection images can be displayed on the display unit 30 or stored in a memory or data storage such as a Picture Archiving and Communication System (PACS), Radiology Information System, and the like. The reconstruction unit or processor 39 reconstructs the projection images into one or more images such as slice images, 2D images, 3D images, digital reconstructed radiographs, and the like.

In FIG. 6, an embodiment of the system is flowcharted. In a step 60, x-ray calibration data is received. The x-ray calibration data can include an air scan calibration projection images, and geometric scan calibration projection images received by the decomposition unit. The x-ray calibration data can include data from one or more sensors such as strain gauges, temperature sensors, positional sensors, and the like received by the measurement unit. The x-ray calibration data can include system wear effects, temperature effects, gantry orientations, expected mechanical drift, system specifications, and manufacturing scans stored and maintained by the reference unit.

The x-ray calibration data is decomposed in a step 62 using a multi-layer decomposition, which generates projection images specific to each element. For example, the air scan projection image of FIG. 2 can be decomposed to generate the projection images of FIG. 4 specific to each element. The projection images of each element can be stored as reference projection images or as updates to existing reference projection images.

In a step 64, the projection images for each element from the decomposition are combined with other x-ray calibration data to determine the reference positions of each element. The reference positions for each element can be represented as graphs such as FIG. 5. The determined reference positions can include translation and rotation for each position in the range of motion of the gantry. The changes in the positions of each element with gantry angle can be stored in the storage device.

In a step 66, subject x-ray data is received. The subject x-ray data includes image projection data with a subject received by the decomposition unit. The subject x-ray data can include data from one or more sensors such as strain gauges, temperature sensors, positional sensors, and the like received by the measurement unit.

The subject x-ray image projection data is decomposed using a multi-layer decomposition in a step 68 similar to the decomposition of the calibration x-ray data. The decomposition generates projection images specific to each element. The system 14 uses the decomposition projection images, subject x-ray data, and reference information from the reference unit 29 such as the reference position of each element to determine the actual position of each element in a step 70. For example, x-ray data of a subject or image regions adjacent to the subject can be decomposed into effects by individual elements based on prior reference scans from the reference unit 29 and current measurements from the measurement unit 37 or based on image-processing methods. Using the lamellae shadows as an example, the lines can be used to compute a relative difference between the estimated lamellae shadow pattern and the actual pattern. The same comparison can be performed for each element to yield a set of variances for the plurality of elements 18.

The actual position of each element can be used to update the reference position in a step 72 or recorded to further analysis on the performance of the system. The comparison of the reference scan adjusted by the measurements can be further adjusted based on decomposition of a projection of a current projection image which includes the subject.

A uniformity correction is generated in a step 74 from the actual position or the reference position of each element. The correction can be dynamically updated during the imaging process such as using the set of variances dynamically with x-ray data of a subject or with retrieval of reference relative positions from the reference unit adjusted with measurements from the measurement unit. The correction can include an intensity adjustment or uniformity correction value. In one embodiment, the corrections are constructed using an overlay for each element which includes a relative adjustment in intensity by each element for a volume location.

In a step 76, reconstruction of a projection image or images with the subject is performed using the subject x-ray data modified with the generated correction. The correction corrects the attenuation used to reconstruct a projection image or images of a subject by correcting for non-uniformity effects in the measurement. The reconstruction reconstructs images such as the 2D projection images into a 3D volume image. Slice images, surface rendering images and the like derived from the 3D volume image can be displayed on a display device and/or stored in a data storage or memory.

A decision step reflects the operation of steps such that calibration scans are periodically performed such as before each patient, daily, weekly, monthly, etc. Even with performing a calibration scan before scanning each subject, one or more scans with the subject or subjects can occur between calibration scans.

It is to be appreciated that in connection with the particular illustrative embodiments presented herein certain structural and/or function features are described as being incorporated in defined elements and/or components. However, it is contemplated that these features may, to the same or similar benefit, also likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular elements or components described herein may have their functionality suitably implemented via hardware, software, firmware or a combination thereof. Additionally, it is to be appreciated that certain elements described herein as incorporated together may under suitable circumstances be stand-alone elements or otherwise divided. Similarly, a plurality of particular functions described as being carried out by one particular element may be carried out by a plurality of distinct elements acting independently to carry out individual functions, or certain individual functions may be split-up and carried out by a plurality of distinct elements acting in concert. Alternately, some elements or components otherwise described and/or shown herein as distinct from one another may be physically or functionally combined where appropriate.

In short, the present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof. That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

What is claimed is:

1. An x-ray computed tomography system, comprising:
    a gantry movable to different orientations to generate x-ray data which includes image projection data at a plurality of the orientations;
    a plurality of elements connected to the gantry which cause x-ray attenuation of the generated image projection data;
    one or more processors programmed to:
        receive the generated x-ray data;
        decompose the received image projection data into indications of relative positions of the plurality of elements at different orientations of the gantry.

2. The x-ray computed tomography system according to claim 1, wherein the plurality of elements include:
    an x-ray source;
    an x-ray filter;
    a shutter/collimator;
    an x-ray detector; and
    an anti-scatter grid.

3. The x-ray computed tomography system according to claim 1, wherein the one or more processors are further programmed to:
    receive x-ray data which includes image projection data and corresponds to the plurality of orientations;
    correct the image projection data at each orientation with a corresponding correction of the measured attenuation based on the relative positions of the plurality of elements at each orientation;
    reconstruct the corrected image projection data into a 3D image representation.

4. The x-ray computed tomography system according to claim 1, wherein the generated x-ray data includes measurements of attenuation attributable to an imaged subject and measurements of attenuation attributable to the plurality of elements, and the measurements of attenuation attributable to the plurality of elements changes with the orientations of the gantry.

5. The x-ray computed tomography system according to claim 1, further including:
    at least one sensor which measures movement of anyone of the plurality of elements, and the generated x-ray data includes the measured movement.

6. The x-ray computed tomography system according to claim 5, wherein the one or more processors are further programmed to analyze the image projection data to measure the movement.

7. The x-ray computed tomography system according to claim 1, wherein the processor is one or more processors are further programmed to:
    generate a series of correction overlays corresponding to relative positions of the plurality of elements, and an alignment of the overlays shift overlaid correction overlays with changes in the relative positions of the plurality of elements.

8. The x-ray computed tomography system according to claim 1, further including:
    a plurality of sensors configured to measure movement of the plurality of elements;
    wherein the one or more processors are further programmed to receive the measurements from the plurality of sensors and compute the relative position of the plurality of elements at different gantry orientations based on the received measurements.

9. The x-ray computed tomography system according to claim 1, further including:
    a reference unit which maintains by gantry orientation for each element of the plurality of elements at least one of:
        air projection images for each element;
        geometric calibration information for each element; and
        relative displacements of each element by design, temperature, system wear indicators, and time.

10. The x-ray computed tomography system according to claim 1, further including:
    a correction unit which performs a correction of measured attenuation in accordance with the decomposed positions of the plurality of elements at each gantry orientation.

11. A method of x-ray computed tomography calibration, comprising:
    receiving x-ray data which includes image projection data at each of a plurality of gantry orientations around an imaging region;
    decomposing the received image projection data to derive relative positions of a plurality of elements at one or more gantry orientations, each of the plurality of elements causing x-ray attenuation attributable to the plurality of elements in the received image projection data; and generating a correction of measured x-ray attenuation based on the relative positions of the plurality of elements.

12. The method according to claim 11, further including:
receiving subject x-ray data which includes subject image projection data from different gantry orientations;
correcting the subject image projection data at each orientation with a corresponding correction based on the relative positions of the plurality of elements;
reconstructing the corrected subject image projection data into a 3D image representation.

13. The method according to claim 11, further including:
performing an air calibration scan to generate air projection reference images by gantry orientation;
performing a geometric calibration scan to measure a relative position of at least an x-ray source and an x-ray detector by gantry orientation;
decomposing the air projection reference images to generate element reference images for at least an x-ray filter, a shutter/collimator, and an anti-scatter grid;
determining a relative position of the x-ray filter, the shutter/collimator, the anti-scatter grid, the x-ray source, and the x-ray detector by gantry orientation based on the decomposed element reference images and the geometric calibration scan;
correcting subject image projection data with a correction for the measured attenuation based on the decomposed relative positions of the x-ray filter, the shutter/collimator, the anti-scatter grid, the x-ray source, and the x-ray detector; and
reconstructing corrected subject image projection data into a 3D image.

14. The method according to claim 11, wherein decomposing includes:
computing a distance and orientation of each element of the plurality of elements relative to a reference position for each gantry orientation based on the air and geometric calibration scans.

15. The method according to claim 11, wherein decomposing further includes:
adjusting the relative position of at least one element of the plurality of elements based on at least one sensor measurement.

16. The method according to claim 11, wherein generating the correction of measured x-ray attenuation includes:
constructing an intensity adjustment to the image projection data for each element of the plurality of elements based on the decomposed relative position of the element.

17. The method according to claim 11, wherein generating a correction of measured x-ray attenuation includes:
constructing correction overlays for each element of the plurality of elements;
shifting the correction overlays in accordance with the relative positions of the elements to form a correction for each gantry orientation.

18. A non-transitory computer-readable storage medium carrying software which controls one or more electronic data processing devices to perform a method according to claim 11.

19. An electronic data processing device configured to perform a method according to claim 11.

20. An x-ray computed tomography system, comprising:
a rotatable gantry carrying elements which include an x-ray source, an x-ray filter, a shutter/collimator, an x-ray detector, and an anti-scatter grid, the rotatable gantry being moveable to different orientations;
a memory which stores contributions to air scan projection images attributable to each of the elements;
a decomposition unit which decomposes the air scan projection images at the different orientations into relative positions of each of the elements;
a correction unit which adjusts a correction to image projection data based on the relative positions of the each of the elements.

* * * * *